(12) United States Patent
Copeland et al.

(10) Patent No.: US 12,364,374 B2
(45) Date of Patent: Jul. 22, 2025

(54) SURFACE CLEANING DEVICE WITH ODOR CONTROL

(71) Applicant: SHARKNINJA OPERATING LLC, Needham, MA (US)

(72) Inventors: Philippa J. Copeland, Hayling Island (GB); Jemima L. C. Meil, Lancaster (GB); Hugh J. Croggon, Newbury (GB); Oliver G. Holmes, London (GB)

(73) Assignee: SharkNinja Operating LLC, Needham, MA (US)

( * ) Notice: Subject to any disclaimer, the term of this patent is extended or adjusted under 35 U.S.C. 154(b) by 307 days.

(21) Appl. No.: 17/980,700

(22) Filed: Nov. 4, 2022

(65) Prior Publication Data
US 2023/0157495 A1    May 25, 2023

Related U.S. Application Data

(60) Provisional application No. 63/276,151, filed on Nov. 5, 2021.

(51) Int. Cl.
*A47L 7/00* (2006.01)
*A47L 9/04* (2006.01)
*C11D 3/00* (2006.01)
*C11D 3/18* (2006.01)
*C11D 3/20* (2006.01)

(52) U.S. Cl.
CPC ............ *A47L 7/009* (2013.01); *A47L 9/0477* (2013.01); *C11D 3/0068* (2013.01); *C11D 3/181* (2013.01); *C11D 3/2086* (2013.01)

(58) Field of Classification Search
CPC ...... C11D 3/0068; C11D 3/181; C11D 3/2086
See application file for complete search history.

(56) References Cited

U.S. PATENT DOCUMENTS

| | | |
|---|---|---|
| 1,446,456 A | 2/1923 | Frazee, Jr. |
| 2,070,643 A | 2/1937 | Becker |
| 4,154,398 A | 5/1979 | Gualandi |
| 4,545,917 A | 10/1985 | Smith et al. |
| 4,554,698 A | 11/1985 | Rennecker et al. |
| D381,477 S | 7/1997 | Ingram |
| 5,766,547 A | 6/1998 | Kay et al. |
| 5,922,093 A | 7/1999 | James et al. |
| 5,946,770 A | 9/1999 | Bijma et al. |

(Continued)

FOREIGN PATENT DOCUMENTS

| | | |
|---|---|---|
| CA | 2467286 | 9/2008 |
| CN | 2801057 | 8/2006 |

(Continued)

OTHER PUBLICATIONS

US Office Action mailed Jan. 5, 2023, received in U.S. Appl. No. 17/846,829, 9 pages.

(Continued)

*Primary Examiner* — C. A. Rivera
(74) *Attorney, Agent, or Firm* — Grossman Tucker Perreault & Pfleger, PLLC

(57) ABSTRACT

A surface cleaning device may include a nozzle, a dust cup, a suction motor configured to draw air into the nozzle and through the dust cup, and a first deodorizer coupled to the nozzle, the first deodorizer includes a deodorizing composition having a long chain fatty acid.

20 Claims, 11 Drawing Sheets

(56) References Cited

U.S. PATENT DOCUMENTS

| | | |
|---|---|---|
| 6,090,184 A | 7/2000 | Cartellone |
| 6,156,088 A | 12/2000 | Cardarelli |
| 6,156,099 A | 12/2000 | Hironaka et al. |
| 6,171,375 B1 | 1/2001 | Howie |
| 6,174,350 B1 | 1/2001 | Rohn et al. |
| 6,295,695 B1 | 10/2001 | Park |
| 6,459,955 B1 | 10/2002 | Bartsch et al. |
| 6,499,183 B1 | 12/2002 | Paterson et al. |
| 6,511,548 B1 | 1/2003 | Oreck et al. |
| 6,589,323 B1 | 7/2003 | Korin |
| 6,802,460 B2 | 10/2004 | Hess et al. |
| 6,941,199 B1 | 9/2005 | Bottomley et al. |
| 7,093,773 B2 | 8/2006 | Kuiper |
| 7,108,731 B2 | 9/2006 | Park et al. |
| 7,305,735 B2 | 12/2007 | Overvaag |
| 7,507,272 B2 | 3/2009 | Emig et al. |
| 7,528,102 B2 | 5/2009 | Barthel et al. |
| 7,628,846 B2 | 12/2009 | Oh et al. |
| 7,765,636 B2 | 8/2010 | Hirota et al. |
| 7,774,897 B2 | 8/2010 | Oh et al. |
| 7,837,772 B2 | 11/2010 | Sepke |
| 7,837,958 B2 | 11/2010 | Crapser et al. |
| 7,958,597 B2 | 6/2011 | Frantzen et al. |
| 8,211,208 B2 | 7/2012 | Chan et al. |
| 8,225,456 B2 | 7/2012 | Håkan et al. |
| 8,857,735 B2 | 10/2014 | Rosener et al. |
| 8,881,999 B2 | 11/2014 | Blaylock et al. |
| 8,984,705 B2 | 3/2015 | Bosses |
| 8,991,003 B2 | 3/2015 | Krebs |
| 9,033,316 B2 | 5/2015 | Hansen et al. |
| 9,433,691 B2 | 9/2016 | Eide et al. |
| 9,585,536 B2 | 3/2017 | Pi et al. |
| 9,649,004 B2 | 5/2017 | Houghton et al. |
| 9,675,220 B2 | 6/2017 | Kah, Jr. |
| 9,717,815 B2 | 8/2017 | Peterson et al. |
| 9,782,049 B2 | 10/2017 | York et al. |
| 9,801,970 B2 | 10/2017 | Chase et al. |
| 9,820,627 B2 | 11/2017 | Caro, Jr. et al. |
| 9,889,220 B1 | 2/2018 | Yip et al. |
| 10,238,253 B2 | 3/2019 | Morrow et al. |
| 10,391,191 B2 | 8/2019 | Cutler et al. |
| 10,398,280 B2 | 9/2019 | Krebs et al. |
| 10,549,005 B2 | 2/2020 | Davis et al. |
| 10,610,612 B2 | 4/2020 | Jakins et al. |
| 10,806,815 B2 | 10/2020 | Hackert |
| 10,827,892 B2 | 11/2020 | Krebs et al. |
| 11,857,138 B2 | 1/2024 | Copeland et al. |
| 2005/0015914 A1 | 1/2005 | You et al. |
| 2005/0022331 A1 | 2/2005 | Kim et al. |
| 2005/0191217 A1 | 9/2005 | Selander |
| 2005/0194460 A1 | 9/2005 | Selander |
| 2006/0090290 A1 | 5/2006 | Lau |
| 2006/0225242 A1 | 10/2006 | Oh et al. |
| 2007/0022560 A1 | 2/2007 | Corwin et al. |
| 2007/0209144 A1 | 9/2007 | Fester et al. |
| 2008/0148512 A1 | 6/2008 | Beskow et al. |
| 2010/0116935 A1 | 5/2010 | Rieger et al. |
| 2010/0175559 A1 | 7/2010 | Sepke |
| 2011/0146720 A1 | 6/2011 | Huffman |
| 2012/0304412 A1 | 12/2012 | Lynch et al. |
| 2013/0058635 A1 | 3/2013 | Vrdoljak |
| 2013/0152337 A1 | 6/2013 | Thorne |
| 2013/0323193 A1* | 12/2013 | Kawano ............... A61Q 15/00 562/595 |
| 2014/0150201 A1 | 6/2014 | McGee et al. |
| 2014/0377130 A1 | 12/2014 | Edwards et al. |
| 2015/0013102 A1 | 1/2015 | Bilger |
| 2015/0040340 A1 | 2/2015 | Bilger et al. |
| 2015/0135474 A1 | 5/2015 | Gidwell |
| 2015/0297054 A1 | 10/2015 | Weeks et al. |
| 2015/0351596 A1 | 12/2015 | Thorne |
| 2016/0128530 A1 | 5/2016 | Thorne et al. |
| 2016/0174793 A1 | 6/2016 | Burke et al. |
| 2016/0220080 A1 | 8/2016 | Thorne |
| 2016/0220081 A1 | 8/2016 | Xu et al. |
| 2016/0220082 A1 | 8/2016 | Thorne et al. |
| 2016/0302631 A1 | 10/2016 | Guerra et al. |
| 2016/0324388 A1 | 11/2016 | Vrdoljak et al. |
| 2016/0374533 A1 | 12/2016 | Innes et al. |
| 2017/0042319 A1 | 2/2017 | Conrad et al. |
| 2017/0112343 A1 | 4/2017 | Innes et al. |
| 2017/0127896 A1 | 5/2017 | Carter et al. |
| 2017/0144810 A1 | 5/2017 | Birdsell |
| 2017/0215667 A1 | 8/2017 | Thorne et al. |
| 2017/0280950 A1 | 10/2017 | Nam et al. |
| 2017/0347848 A1 | 12/2017 | Carter et al. |
| 2018/0035854 A1 | 2/2018 | Thorne |
| 2018/0055320 A1 | 3/2018 | Hwang et al. |
| 2018/0064301 A1 | 3/2018 | Cottrell et al. |
| 2018/0068815 A1 | 3/2018 | Cottrell |
| 2018/0070785 A1 | 3/2018 | Udy et al. |
| 2018/0125314 A1 | 5/2018 | Kim et al. |
| 2018/0255991 A1 | 9/2018 | Der Marderosian et al. |
| 2018/0296046 A1 | 10/2018 | Thorne et al. |
| 2018/0306432 A1 | 10/2018 | Ognjen et al. |
| 2018/0325252 A1 | 11/2018 | Hopke et al. |
| 2018/0333736 A1 | 11/2018 | Krebs |
| 2018/0338654 A1 | 11/2018 | Kelsey |
| 2018/0338656 A1 | 11/2018 | Carter et al. |
| 2019/0022269 A1* | 1/2019 | Hackert ............... A47L 7/009 |
| 2019/0038098 A1 | 2/2019 | Thorne et al. |
| 2019/0059668 A1 | 2/2019 | Thorne et al. |
| 2019/0069740 A1 | 3/2019 | Thorne et al. |
| 2019/0069744 A1 | 3/2019 | Liggett et al. |
| 2019/0090701 A1 | 3/2019 | Tonderys et al. |
| 2019/0090705 A1 | 3/2019 | Thorne et al. |
| 2019/0117030 A1 | 4/2019 | Kette |
| 2019/0133391 A1 | 5/2019 | Khazaieli et al. |
| 2019/0191947 A1 | 6/2019 | Freese et al. |
| 2019/0193120 A1 | 6/2019 | Brown et al. |
| 2019/0246853 A1 | 8/2019 | Sardar et al. |
| 2019/0274500 A1 | 9/2019 | Thorne et al. |
| 2019/0274501 A1 | 9/2019 | Antonisami et al. |
| 2019/0302793 A1 | 10/2019 | Leech et al. |
| 2019/0320861 A1 | 10/2019 | Conrad |
| 2019/0320865 A1 | 10/2019 | Brown et al. |
| 2019/0320866 A1 | 10/2019 | Thorne et al. |
| 2019/0335968 A1 | 11/2019 | Harting et al. |
| 2019/0343349 A1 | 11/2019 | Clare et al. |
| 2019/0357740 A1 | 11/2019 | Thorne et al. |
| 2020/0000298 A1 | 1/2020 | Brown et al. |
| 2020/0022543 A1 | 1/2020 | Gill et al. |
| 2020/0022544 A1 | 1/2020 | Gill et al. |
| 2020/0022553 A1 | 1/2020 | Gill et al. |
| 2020/0037833 A1 | 2/2020 | Niedzwecki et al. |
| 2020/0037843 A1 | 2/2020 | Fiebig et al. |
| 2020/0046184 A1 | 2/2020 | Freese et al. |
| 2020/0077855 A1 | 3/2020 | Brown et al. |
| 2020/0085267 A1 | 3/2020 | Thorne et al. |
| 2020/0085269 A1 | 3/2020 | Thorne |
| 2020/0121144 A1 | 4/2020 | Gacin et al. |
| 2020/0121148 A1 | 4/2020 | Hoffman et al. |
| 2020/0138260 A1 | 5/2020 | Sutter et al. |
| 2020/0166949 A1 | 5/2020 | Leech et al. |
| 2020/0170470 A1 | 6/2020 | Liggett et al. |
| 2020/0201348 A1 | 6/2020 | Leech |
| 2020/0205631 A1 | 7/2020 | Brown et al. |
| 2020/0205634 A1 | 7/2020 | Sutter et al. |
| 2020/0237171 A1 | 7/2020 | Xu et al. |
| 2020/0288929 A1 | 9/2020 | Brunner |
| 2020/0288930 A1 | 9/2020 | Wells |
| 2020/0297172 A1 | 9/2020 | Tonderys et al. |
| 2020/0301430 A1 | 9/2020 | Irkliy et al. |
| 2020/0315418 A1 | 10/2020 | Howard et al. |
| 2020/0331326 A1 | 10/2020 | Bourne |
| 2020/0345196 A1 | 11/2020 | Innes et al. |
| 2020/0367711 A1 | 11/2020 | Thorne et al. |
| 2020/0371526 A1 | 11/2020 | Kamada |
| 2020/0383547 A1 | 12/2020 | Sutter et al. |
| 2021/0007569 A1 | 1/2021 | Howard et al. |
| 2021/0022574 A1 | 1/2021 | Harting |
| 2021/0030227 A1 | 2/2021 | Mathieu et al. |
| 2021/0038032 A1 | 2/2021 | Brown |
| 2021/0052121 A1 | 2/2021 | Kim et al. |

(56) References Cited

U.S. PATENT DOCUMENTS

| | | |
|---|---|---|
| 2021/0059495 A1 | 3/2021 | Gill et al. |
| 2021/0085144 A1 | 3/2021 | Woodrow et al. |
| 2021/0145231 A1 | 5/2021 | Conrad |
| 2021/0161350 A1 | 6/2021 | Nguyen |
| 2021/0169289 A1 | 6/2021 | Thorne et al. |
| 2021/0175772 A1 | 6/2021 | Aini |
| 2021/0177223 A1 | 6/2021 | Der Marderosian et al. |
| 2021/0186282 A1 | 6/2021 | Mathieu et al. |
| 2021/0204684 A1 | 7/2021 | Heman-Ackah et al. |
| 2021/0254615 A1 | 8/2021 | Vrdoljak et al. |
| 2021/0307581 A1 | 10/2021 | Thorne et al. |
| 2021/0315428 A1 | 10/2021 | Udy et al. |
| 2021/0386261 A1 | 12/2021 | Woodrow et al. |
| 2021/0386262 A1 | 12/2021 | Uchendu et al. |
| 2022/0031131 A1 | 2/2022 | McClay et al. |
| 2022/0031133 A1 | 2/2022 | Der Marderosian et al. |
| 2022/0031134 A1 | 2/2022 | Yang et al. |
| 2022/0039622 A1 | 2/2022 | Kim et al. |
| 2022/0061614 A1 | 3/2022 | Yu et al. |
| 2022/0071459 A1 | 3/2022 | Gacin et al. |
| 2022/0095864 A1 | 3/2022 | Der Marderosian et al. |
| 2022/0125256 A1 | 4/2022 | Lessard et al. |
| 2022/0287521 A1 | 9/2022 | Cottrell et al. |
| 2022/0322903 A1 | 10/2022 | Lessard |
| 2022/0400922 A1 | 12/2022 | McClay et al. |
| 2022/0408994 A1 | 12/2022 | Hill |
| 2023/0012532 A1 | 1/2023 | Kim et al. |
| 2023/0043567 A1 | 2/2023 | Copeland et al. |
| 2023/0070147 A1 | 3/2023 | Harting et al. |
| 2023/0132447 A1 | 5/2023 | Kim et al. |
| 2023/0141469 A1 | 5/2023 | Gill et al. |
| 2023/0146588 A1 | 5/2023 | Kim et al. |
| 2023/0157495 A1 | 5/2023 | Copeland et al. |
| 2023/0248192 A1 | 8/2023 | Brown et al. |
| 2023/0320550 A1 | 10/2023 | Teuscher et al. |
| 2023/0329502 A1 | 10/2023 | Chirikjian |
| 2023/0355065 A1 | 11/2023 | Finnegan |
| 2023/0414052 A1 | 12/2023 | McClay et al. |
| 2024/0008699 A1 | 1/2024 | Innes et al. |
| 2024/0415352 A1 | 12/2024 | McClay et al. |

FOREIGN PATENT DOCUMENTS

| | | | |
|---|---|---|---|
| CN | 101703383 | 5/2010 | |
| CN | 209236011 | 8/2019 | |
| CN | 209270405 | 8/2019 | |
| CN | 209316598 | 8/2019 | |
| CN | 111971077 | 11/2020 | |
| CN | 216135772 | 3/2022 | |
| CN | 115316883 | 11/2022 | |
| DE | 8028824 | 3/1981 | |
| DE | 29712553 | 9/1997 | |
| DE | 102007060847 | 9/2013 | |
| DE | 102015118653 | 5/2017 | |
| DE | 202017103530 | 9/2017 | |
| DE | 202018004401 | 1/2019 | |
| DE | 202020102190 | 6/2020 | |
| DE | 102019122968 A1 * | 3/2021 | |
| EP | 1201173 | 8/2004 | |
| EP | 1482825 | 6/2006 | |
| EP | 2623007 A2 * | 8/2013 | ............ A47L 11/34 |
| EP | 3682910 | 7/2020 | |
| FR | 2833531 | 6/2003 | |
| GB | 2422777 | 8/2006 | |
| GB | 2407967 | 4/2007 | |
| JP | H10151097 | 6/1998 | |
| JP | 2004113469 | 4/2004 | |
| JP | 2008036151 | 2/2008 | |
| JP | 2013000480 | 1/2013 | |
| KR | 20050085102 A * | 8/2005 | |
| KR | 1020140111819 | 9/2014 | |
| KR | 20210002057 | 1/2021 | |
| WO | 2006108320 | 10/2006 | |

OTHER PUBLICATIONS

Chinese Office Action with English language Summary, issued Feb. 7, 2023, received in Chinese Patent Application No. 202222938452. 7, 4 pages.
PCT Search Report and Written Opinion received in PCT Application No. PCT/US22/48954, 12 pages.
U.S. Office Action issued Jun. 27, 2024, received in U.S. Appl. No. 18/525,522, 17 pages.
PCT Search Report and Written Opinion mailed Sep. 26, 2023, received in PCT Application No. PCT/US2023/026292, 9 pages.
Chinese Office Action with machine-generated translation issued Dec. 14, 2023, received in Chinese Patent Application No. 202321757693.X, 5 pages.
Operating Manual of Gtech 5254 AirRAM Platinum; Grey Technology Limited, Retrieved Jul. 3, 2022, 20 pages.
AirRam Platinum, Anti Hair Wrap Cordless Vacuum, Gtech, 2022, https://www.gtech.co.uk/cordless-vacuum-cleaners/uprights/airram-platinum.html.
PCT Search Report and Written Opinion mailed May 30, 2023, received in PCT Application No. PCT/US23/14632, 8 pages.
U.S. Office Action issued May 9, 2023, received in U.S. Appl. No. 17/846,829, 9 pages.
U.S. Office Action issued Sep. 10, 2024, received in U.S. Appl. No. 17/857,639, 11 pages.
PCT Search Report and Written Opinion mailed Sep. 20, 2024, received in PCT Application No. PCT/US2024/035205, 13 pages.

* cited by examiner

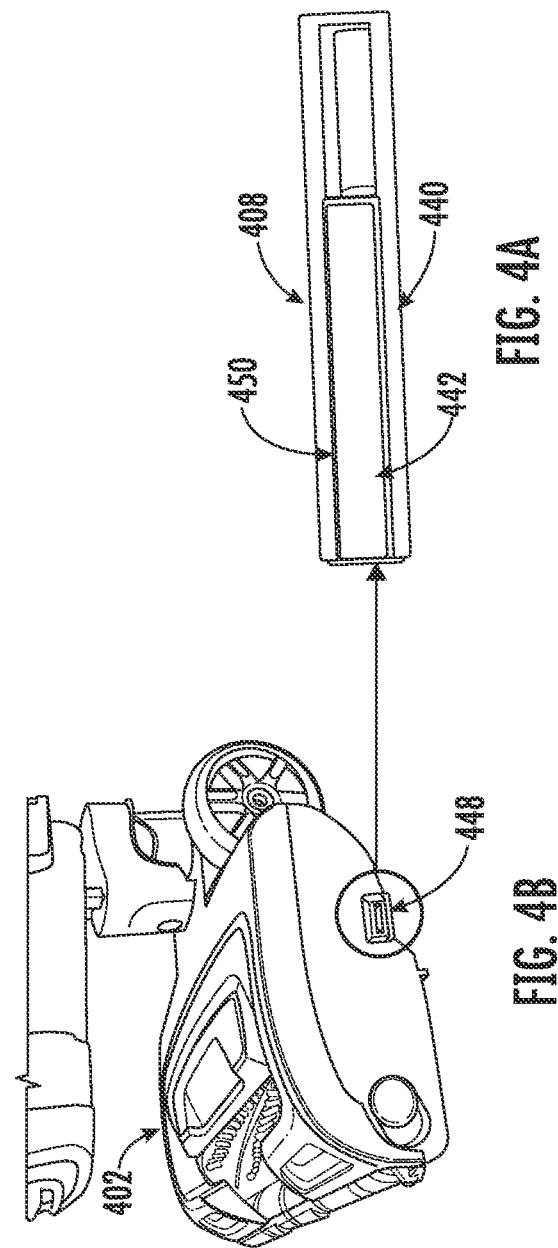

| MALODOR<br>CHEMICAL CLASS | DOG SMELL | CAT SMELL | BODY SMELL | CIGARETTE SMELL | MILDEW SMELL | BATHROOM SMELL | GARBAGE SMELL |
|---|---|---|---|---|---|---|---|
| MOLECULES CONTAINING SULFUR | X | XXX | X | | | XXX | XX |
| MOLECULES CONTAINING NITROGEN | | XXX | XXX | XXX | | XXX | XX |
| MOLECULES CONTAINING CARBOXYLIC ACID GROUPS | X | X | X | XX | XXX | | XXX |
| MOLECULES CONTAINING CARBONYL GROUPS OR ALCOHOL GROUPS | XXX | | | | XXX | X | XX |

| | |
|---|---|
| 1 | STEARIC ACID 100% |
| 2 | SOY WAX 20% STEARIC ACID 80% |
| 3 | SOY WAX 50% STEARIC ACID 50% |
| 4 | SOY WAX 100% |
| 5 | SOY WAX 50% ZINC RICINOLEATE 50% |
| 6 | SOY WAX 90% ZINC RICINOLEATE 10% |
| 7 | SOY WAX 99% ZINC RICINOLEATE 1% |
| 8 | STEARIC ACID 90% ZINC RICINOLEATE 10% |
| 9 | STEARIC ACID 99% ZINC RICINOLEATE 1% |
| 10 | ZINC RICINOLEATE 100% |
| 11 | CETEARYL ALCOHOL 99% ZINC RICINOLEATE 1% |
| 12 | CETEARYL ALCOHOL 90% ZINC RICINOLEATE 10% |
| 13 | CETEARYL ALCOHOL 50% STEARIC ACID 50% |
| 14 | CETEARYL ALCOHOL 20% STEARIC ACID 80% |
| 15 | SOY WAX 90% CETEARYL ALCOHOL 10% |
| 16 | SOY WAX 80% CETEARYL ALCOHOL 20% |
| 17 | SOY WAX 50% CETEARYL ALCOHOL 50% |
| 18 | SOY WAX 20% CETEARYL ALCOHOL 80% |
| 19 | SOY WAX 10% CETEARYL ALCOHOL 90% |
| 20 | PARAFFIN WAX 100% |
| 21 | PARAFFIN WAX 10% STEARIC ACID 90% |
| 22 | PARAFFIN WAX 20% STEARIC ACID 80% |
| 23 | PARAFFIN WAX 50% STEARIC ACID 50% |
| 24 | PARAFFIN WAX 99% STEARIC ACID 1% |
| 25 | PARAFFIN WAX 90% STEARIC ACID 10% |
| MA1 | STEARIC ACID 100% (PORTION 1) <br> ZINC RICINOLEATE 100% (PORTION 2) |
| MA2 | SOY WAX 20% STEARIC ACID 80% (PORTION 1) <br> SOY WAX 90% ZINC RICINOLEATE 10% (PORTION 2) |
| MA3 | PARAFFIN WAX 10% STEARIC ACID 90% (PORTION 1) <br> PARAFFIN WAX 90% ZINC RICINOLEATE 10% (PORTION 2) |

*MA - MULTI ACTION

FIG. 13

| STERIC ACID: SOY WAX | BEFORE | AFTER | DIFFERENCE | EXTRAPOLATED 6 MONTH USE (15hrs) | EXTRAPOLATED RATE OF USE |
|---|---|---|---|---|---|
| 80:20 | 14.93g | 14.84g | 0.09g | 8.1g | 0.54g/hr |
| 50:50 | 16.39g | 15.97g | 0.42g | 37.8g | 2.52g/hr |
| 100:0 | 13.30g | 13.29g | 0.01g | 0.9g | 0.06g/hr |

FIG. 14

SURFACE CLEANING DEVICE WITH ODOR CONTROL

CROSS-REFERENCE TO RELATED APPLICATIONS

The present application claims the benefit of U.S. Provisional Application Ser. No. 63/276,151 filed on Nov. 5, 2021, entitled Surface Cleaning Device with Odor Control, which is fully incorporated herein by reference.

TECHNICAL FIELD

The present disclosure is generally directed to surface cleaning devices and, more particularly to, a surface cleaning device including a deodorizer.

BACKGROUND INFORMATION

The following is not an admission that anything discussed below is part of the prior art or part of the common general knowledge of a person skilled in the art.

Powered surface cleaning devices, such as vacuum cleaners, have multiple components that each receive electrical power from one or more power sources (e.g., one or more batteries or electrical mains). For example, a vacuum cleaner may include a suction motor to generate a vacuum within a nozzle. The generated vacuum collects debris from a surface to be cleaned and deposits the debris, for example, in a dust cup. The vacuum may also include a motor to rotate a brush roll within the nozzle. The rotation of the brush roll agitates debris that has adhered to the surface to be cleaned such that the generated vacuum is capable of removing the debris from the surface. In addition to electrical components for cleaning, the vacuum cleaner may include one or more light sources to illuminate an area to be cleaned.

BRIEF DESCRIPTION OF THE DRAWINGS

These and other features advantages will be better understood by reading the following detailed description, taken together with the drawings wherein:

FIG. 4A shows an example deodorizer consistent with aspects of the present disclosure. FIG. 4B shows the deodorizer being installed within a nozzle and may be an example of the deodorizer and nozzle of FIG. 2.

FIG. 13 is a table enumerating various example compositions for use as or in a deodorizer consistent with aspects of the present disclosure.

FIG. 14 is a table demonstrating relative durability between a plurality of different configurations for a deodorizer consistent with aspects of the present disclosure.

Figure 1:
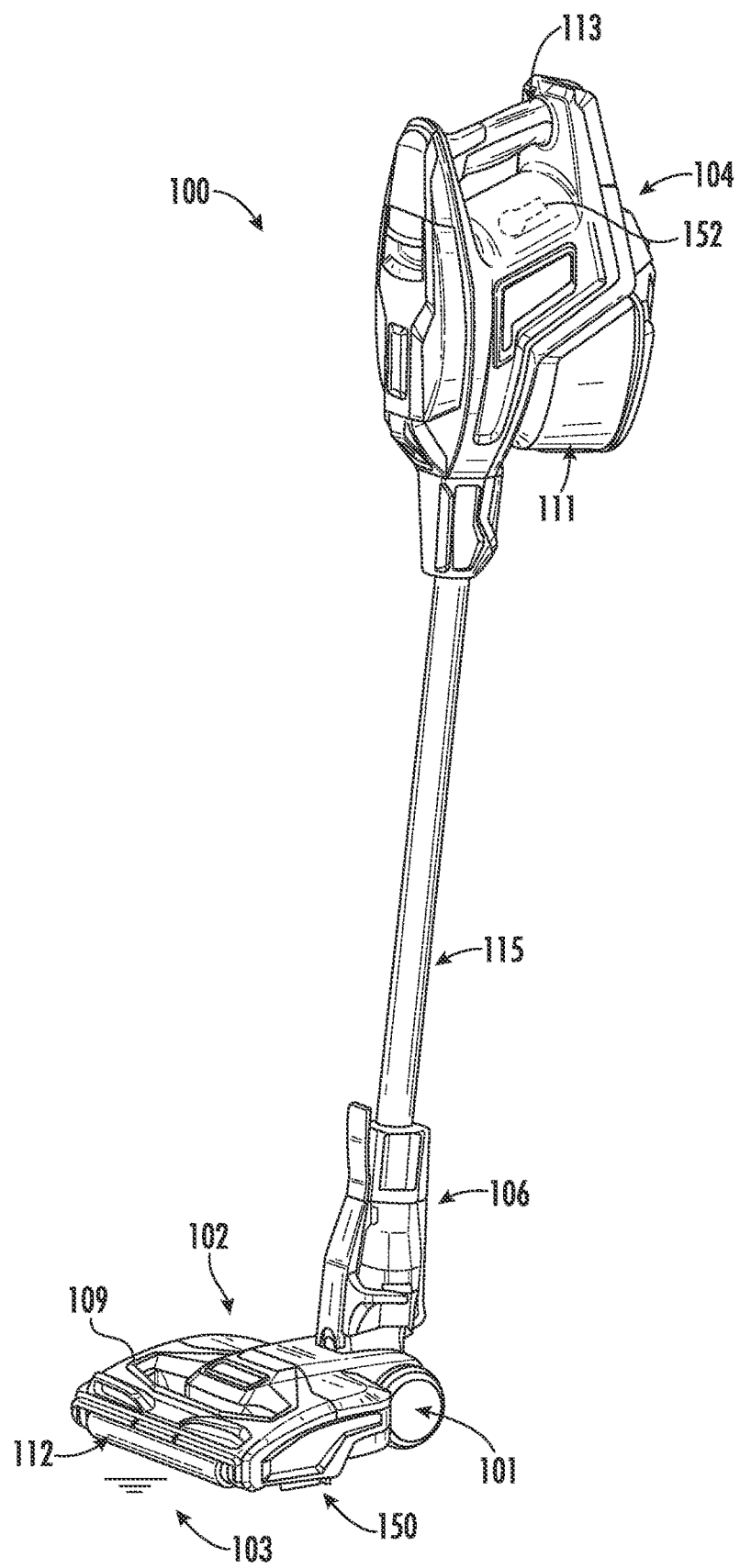
FIG. 1 shows an example surface cleaning device consistent with aspects of the present disclosure.

The drawings included herewith are for illustrating various examples of articles, methods, and apparatuses of the teaching of the present specification and are not intended to limit the scope of what is taught in any way. Like reference numerals refer to like parts throughout the various views unless otherwise specified.

DETAILED DESCRIPTION

The present disclosure is generally directed to a surface cleaning device configured to include a deodorizer for odor control/conditioning during operation of the surface cleaning device. The deodorizer may include a compound formed of a long chain fatty acid such as stearic acid. The deodorizer can be coupled to the surface cleaning device at a location where the deodorizer is agitated during operation of the surface cleaning device. For example, the deodorizer can be positioned to (directly) engage/contact a surface to be cleaned such that friction therebetween causes particles of the deodorizer (e.g., particles formed of long chain fatty acid molecules) to be released from the deodorizer. Alternatively, or in addition, the deodorizer can be positioned to (directly) engage/contact a cleaning element (e.g., a rotating agitator such as a brush roll or foam roller) such that contact between the cleaning element and the deodorizer causes particles of the deodorizer to be released from the deodorizer.

FIG. 1 shows an example surface cleaning device 100. As shown, the surface cleaning device 100 is illustrated as stick-type vacuum. However, aspects and features of the present disclosure may also be implemented in other vacuum types including, for example, hand-held vacuums, robotic vacuums, upright vacuums, cannister vacuums, and/or any other type of vacuum cleaner.

As shown, the surface cleaning device 100 includes a nozzle 102, a motor housing 104 having a suction motor 152, a dust cup 111, and an upright section 106. The nozzle 102 includes a nozzle housing 109, one or more wheels 101, at least one cleaning element 112 (e.g., a brush roll or foam roller), and a dirty air inlet 150. The one or more wheels 101 are configured to enable a user to roll the nozzle 102 across a surface to be cleaned 103 (e.g., according to a push/pull motion). In some instances, the nozzle 102 may include a plurality of cleaning elements 112 configured to rotate, wherein at least one cleaning element 112 is different from at least one other cleaning element 112. For example, a first cleaning element 112 may be a brush roll and a second cleaning element 112 may be a foam roller.

The dirty air inlet 150 is fluidly coupled to a dirty air passageway. The dirty air passageway can be defined, at least in part, by the nozzle housing 109, the upright section 106, a conduit/wand 115, and the dust cup 111. The dust cup 111 can be removably coupled to the motor housing 104. The suction motor 152 is configured to cause air having debris entrained therein to flow along the dirty air passageway. In other words, the suction motor 152 is configured to draw air into the nozzle 102 and through the dust cup 111. At least a portion of the entrained debris may fall out of entrainment when the air is passing through the dust cup 111 and be collected within the dust cup 111 for later disposal.

The at least one cleaning element 112 is configured to (directly) engage the surface to be cleaned 103 during cleaning operations. The at least one cleaning element 112 can be configured to rotate about a longitudinal axis of the rotatable cleaning element 112. The at least one cleaning element 112 may be configured to be driven via a brush roll motor (not shown) and/or can be configured to be driven via manual movement based on a user supplying a push/pull force to the surface cleaning device 100 via a handle 113.

The at least one cleaning element 112 can be configured to (directly) engage a deodorizer consistent with the present disclosure, as discussed in further detail below.

Figure 2:
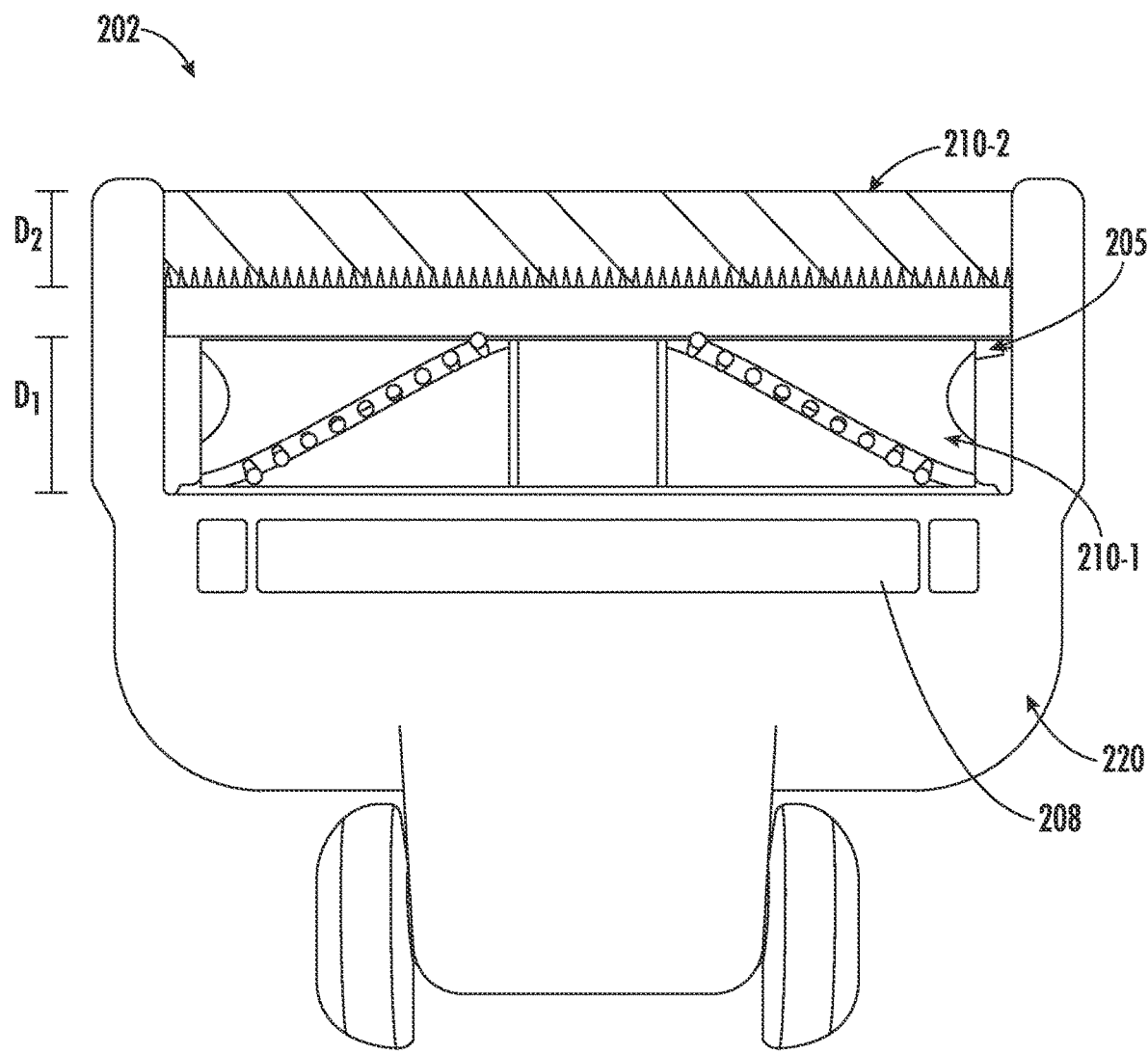
FIG. 2 shows an example nozzle suitable for use within the surface cleaning device of FIG. 1.

FIG. 2 shows a schematic example of a nozzle 202. The nozzle 202 is an example of the nozzle 102 of FIG. 1. As shown, the nozzle 202 includes a bottom surface 220 that faces a surface to be cleaned (e.g., the surface to be cleaned 103 of FIG. 1), first and second cleaning elements 210-1 and 210-2, and a dirty air inlet 205. The dirty air inlet 205 is at least partially defined in the bottom surface 220. In operation, at least a portion of one or more of the first and second cleaning elements 210-1 and 210-2 may extend from the dirty air inlet 205 in a direction of the surface to be cleaned.

The first cleaning element 210-1 can extend substantially parallel with the second cleaning element 210-2. The first cleaning element 210-1 may be a first type of cleaning element and the second cleaning element 210-2 may be a second type of cleaning element, with the first and second types of cleaning elements being different. For example, the first cleaning element 210-1 can be a brush roll having bristles to engage the surface to be cleaned, such as the bristles 321 shown in FIG. 3, and the second cleaning element 210-2 can be a foam roller to engage the surface to be cleaned, such as the foam roller 323 shown in FIG. 3.

The first cleaning element 210-1 may include a first material such as thermoplastic. In one example, the first cleaning element 210-1 includes relatively thin bristles formed of a material such as nylon. The diameter of the bristles may be in a range of 0.04±0.02 mm. The second cleaning element 210-2 may include a second material such as thermoplastic with nylon bristles, for example.

The first cleaning element 210-1 may have an overall diameter D1 that is greater than an overall diameter D2 of the second cleaning element 210-2. The first cleaning element 210-1 may have an overall diameter in a range of 15 millimeters (mm) to 30 mm. The second cleaning element 210-2 may have an overall diameter in a range of 30 mm to 60 mm.

While the nozzle 202 is shown as including a first and second cleaning element 210-1 and 210-2, other configurations are possible. For example, the nozzle 202 may include only one of the first or second cleaning elements 210-1 or 210-2. By way of further example, the nozzle 202 may include one or more additional cleaning elements in addition to the cleaning elements 210-1 and 210-2.

The nozzle 202 may further include a deodorizer 208 coupled to the bottom surface 220. The deodorizer 208 can extend in parallel with the first cleaning element 210-1 and/or the second cleaning element 210-2.

The deodorizer 208 extends from the bottom surface 220 in a direction of the surface to be cleaned by an extension distance. The extension distance may be, for example, in a range between 0 mm and 20 mm. The extension distance may be greater than or equal to the overall distance that the first cleaning element 210-1 and/or the second cleaning element 210-2 extend from the bottom surface 220 of the nozzle 202. Such a configuration may encourage the deodorizer 208 to (directly) engage with the surface to be cleaned during cleaning operations. This configuration may also be referred to herein as a direct application configuration.

Figure 3:
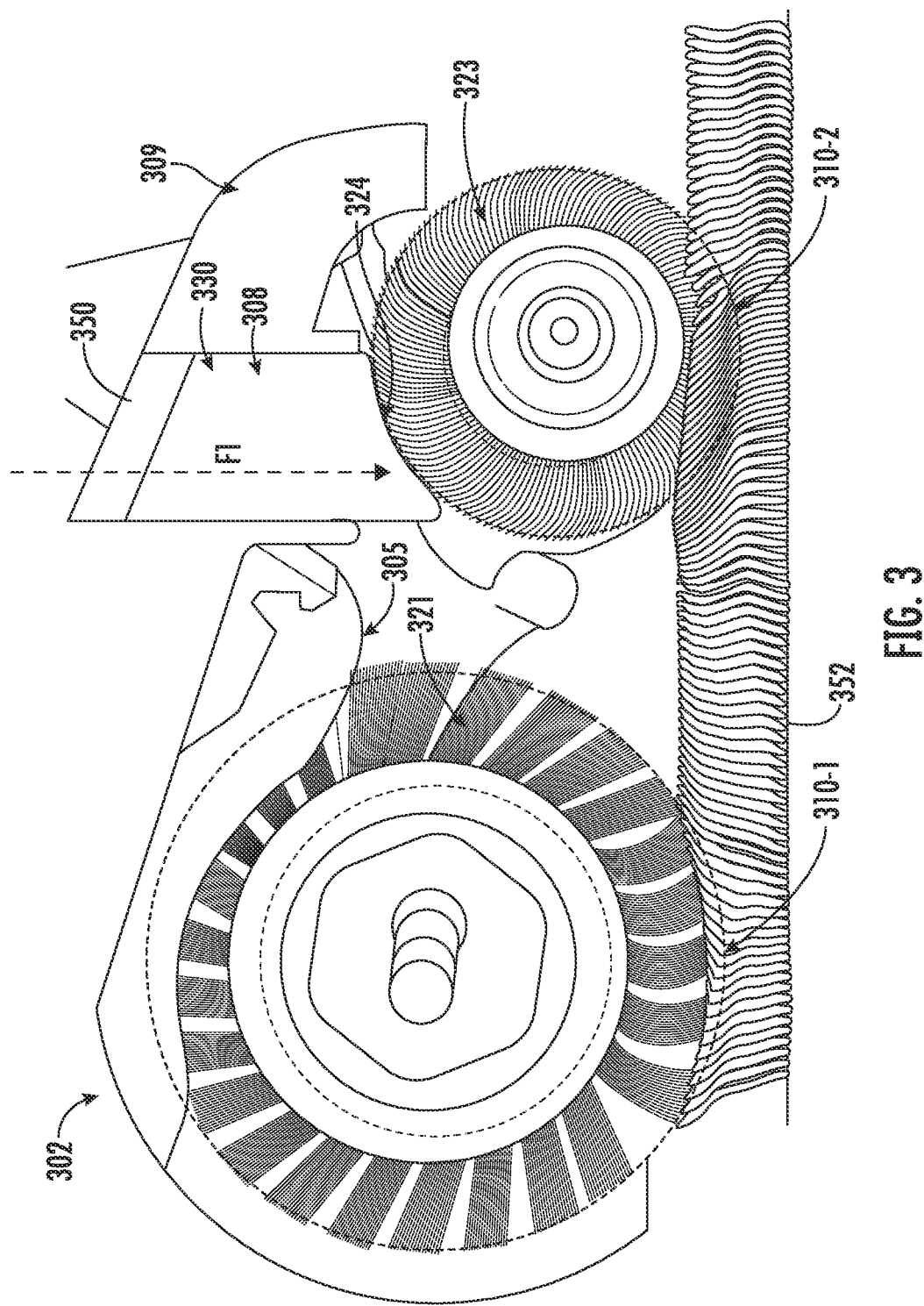
FIG. 3 shows a cross-sectional view of a nozzle suitable for use within the surface cleaning device of FIG. 1 consistent with aspects of the present disclosure.

FIG. 3 shows a cross-sectional view of a nozzle 302, which is an example of the nozzle 102. As shown, the nozzle 302 includes a nozzle housing 309, a first cleaning element 310-1 implemented as a brush roll having bristles 321 extending therefrom, and a second cleaning element 310-2 implemented as a foam roller which is configured to (directly) engage a deodorizer 308. This configuration may also be referred to herein as an indirect applicator configuration. Alternatively, or in addition, the deodorizer 308 can be configured to extend to a distance that causes the deodorizer 308 to also contact/engage (directly) a surface to be cleaned. This configuration may be referred to herein as a dual applicator configuration.

As shown, the deodorizer 308 is disposed in a cavity/receptacle 330 defined by the nozzle housing 309. A biasing mechanism 350 (e.g., a spring) may be disposed within the cavity/receptacle 330 at a location between the nozzle housing 309 and the deodorizer 308. The biasing mechanism 350 may be configured to supply a force F1 that urges the deodorizer 308 in a direction of the second cleaning element 310-2. For example, the force F1 may extend transverse to (e.g., substantially perpendicular to) a surface to be cleaned 352. Such a configuration may allow the deodorizer 308 to remain in (direct) engagement with the second cleaning element 310-2. In some instances, a weight of the deodorizer 308 may be such that the deodorizer 308 remains in (direct) engagement with the second cleaning element 310-2. Such a configuration may omit the biasing mechanism 350.

As shown, the deodorizer 308 defines an engagement surface 324 for (directly) engaging an outer surface of the second cleaning element 310-2. The engagement surface 324 can include a shape/profile that corresponds with the shape/profile of the second cleaning element 310-2. The engagement surface 324 can include this shape/profile when manufactured, or the engagement surface 324 can be introduced via mechanical friction caused between the deodorizer 308 and the second cleaning element 310-2.

The deodorizer 308 is configured to release particles of a deodorizing composition based on the engagement surface 324 (directly) engaging the outer surface of the second cleaning element 310-2. The released particles are configured to couple to the outer surface of the second cleaning element 310-2 and/or be released into the surrounding area. In either case, released particles may then be introduced/transferred to the surface to be cleaned 352. Alternatively, or in addition, released particles may be drawn into the dirty air passageway 305. This can reduce malodors within the dust cup, and also allow for released particles to be exhausted via an outlet of the surface cleaning device.

FIG. 4A shows an example deodorizer 408 consistent with aspects of the present disclosure. The deodorizer 408 may be one example of the deodorizer 208 of FIG. 2 and/or the deodorizer 308 of FIG. 3. FIG. 4B shows the deodorizer 408 being installed within a nozzle 402 and may be an example of the deodorizer 208 and nozzle 202 of FIG. 2.

The deodorizer 408 includes a cartridge body 440 configured to removably couple with the nozzle 402 and a deodorizing composition (or deodorant) 442 coupled to the cartridge body 440. For example, the cartridge body 440 may define a cavity/receptacle 450 configured to receive at least a portion of the deodorizing composition 442. The deodorizing composition 442 may be configured to extend from an open end of the cavity/receptacle 450. The cartridge body 440 may be formed from a material such as a thermoplastic, e.g., acrylonitrile butadiene styrene (ABS).

As shown, the cartridge body 440 may have a length that is equal to or greater than half of a length of a cleaning element rotatably coupled to the nozzle 402 (e.g., the first and/or second cleaning elements 210-1, 210-2, 310-1, and/or 310-2 of FIGS. 2 and 3). Such a configuration may allow the deodorizer 408 to engage (directly) at least half of the cleaning element. For example, the cartridge body 440 may have an elongated profile (e.g., having a length that is greater than a width).

The deodorizing composition 442 includes one or more odor reducing materials, such as but not limited to one or more long chain fatty acids. In examples, the odor reducing material(s) are or include a C12-C20 fatty acid, such as stearic acid (a C18 fatty acid) as discussed in further detail below.

As shown in FIG. 4B, the nozzle 402 includes a cartridge receptacle 448. The cartridge receptacle 448 is configured such that the deodorizer 408 can be slidably inserted therein. The cartridge receptacle 448 can be configured to align the deodorizer 408 with a surface to be cleaned such as shown and described above regarding FIG. 2. The cartridge receptacle 448 may also be disposed at other locations along the nozzle such as at a position that aligns the inserted deodorizer 408 with an associated cleaning element, e.g., the second cleaning element 310-2 as shown in FIG. 3. In one example, a nozzle can include a plurality of cartridge receptacles 448, with each cartridge receptacle 448 configured to align an inserted deodorizer 408 with an associated cleaning element and/or the surface to be cleaned. Alignment of the deodorizer refers to the deodorizer 408 being disposed at a location that causes the deodorizer 408 (e.g., the deodorizing composition 442) to be (directly) engaged/contacted by the associated cleaning element and/or surface to be cleaned.

Figure 5A:
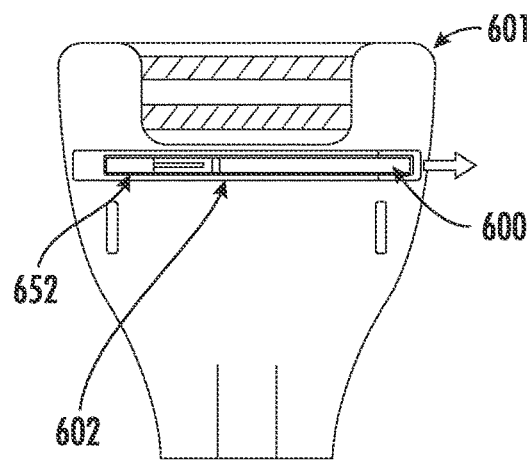
FIG. 5A shows another example nozzle of a surface cleaning device implemented with a deodorizer consistent with aspects of the present disclosure.
Figure 5B:
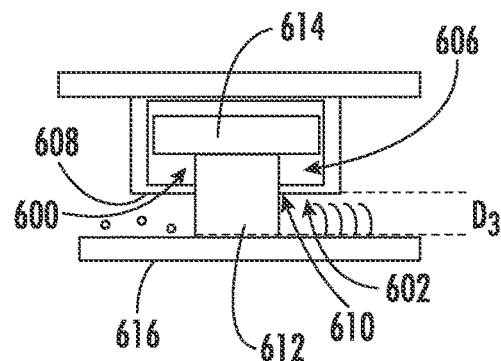
FIG. 5B shows a side view of a nozzle coupled to a deodorizer consistent with aspects of the present disclosure.
Figure 5C:
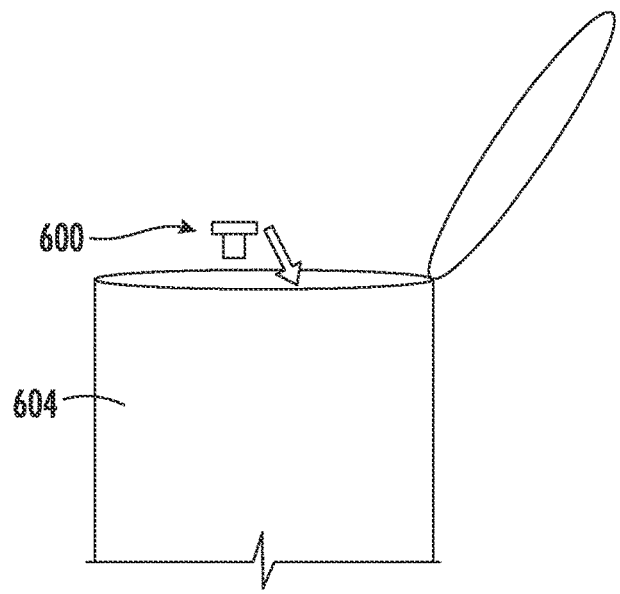
FIG. 5C shows an example disposable deodorizer consistent with aspects of the present disclosure.

FIGS. 5A and 5B show an example of a deodorizer 600, wherein a portion of the deodorizer is configured to be selectively received within a receptacle 602 of a nozzle 601. The deodorizer 600 is an example of the deodorizer 408 of FIG. 4 and the receptacle 602 is an example of the cartridge receptacle 448 of FIG. 4. FIG. 5C shows the deodorizer 600 removed from the receptacle 602 (e.g., for disposal in a trash receptacle 604).

As shown in FIGS. 5A and 5B, the deodorizer 600 can be selectively received within the receptacle 602. As shown, the receptacle 602 defines a receiving region 606. The receiving region 606 includes retaining flanges 608, wherein a passthrough 610 extends between the retaining flanges 608. When the deodorizer 600 is received within the receptacle 602 at least a portion of the deodorizer 600 (e.g., a deodorizing composition, or deodorant, 612 of the deodorizer 600) extends through the passthrough 610 and the retaining flanges 608 may (directly) engage at least a portion of the deodorizer 600 (e.g., a cartridge body 614 of the deodorizer 600) to retain at least a portion of the deodorizer 600 within the receptacle 602. As shown, the deodorizing composition 612 extends through the passthrough 610 and into (direct) engagement with a surface to be cleaned 616. For example, the deodorizing composition 612 may extend from the passthrough by an extension distance D3. The extension distance D3 may be in a range of, for example, 0 mm and 20 mm.

In some instances, a plurality of deodorizers 600 may be coupled to the nozzle 601. For example, the nozzle 601 may include a plurality of receptacles 602, each configured to receive a respective deodorizer 600. At least one of the plurality of deodorizers 600 may be configured to (directly) engage the surface to be cleaned (or a cleaning element). For example, a first receptacle 602 may be configured to position a first deodorizer 600 to (directly) engage a surface to be cleaned (e.g., similar to as shown in FIG. 2) and a second receptacle 602 may be configured to position a second deodorizer 600 to (directly) engage a cleaning element (e.g., similar to as shown in FIG. 3).

The deodorizer 600 can be removed from the receptacle 602. For example, the receptacle 602 may include a latch 652, wherein, in response to actuation of the latch 652, the deodorizer 600 can be removed from the receptacle 602. The latch 652 may be configured to transition between a retaining position and a release position, wherein, when in the retaining position, a portion of the latch 652 is (directly) engaging the deodorizer 600. In some instances, the latch 652 can be biased towards the retaining position.

As shown in FIG. 5C, in response to actuation of the latch 652, the deodorizer 600 can be removed from the receptacle and disposed of by a user. A replacement deodorizer may then be inserted into the receptacle 602. The deodorizer 600 is configured to be disposed of after a predetermined period of use. The predetermined period of use may be, for example, in a range of 10 to 30 operating hours. By way of further example, the predetermined period of use may be at least 15 operating hours.

Figure 6:
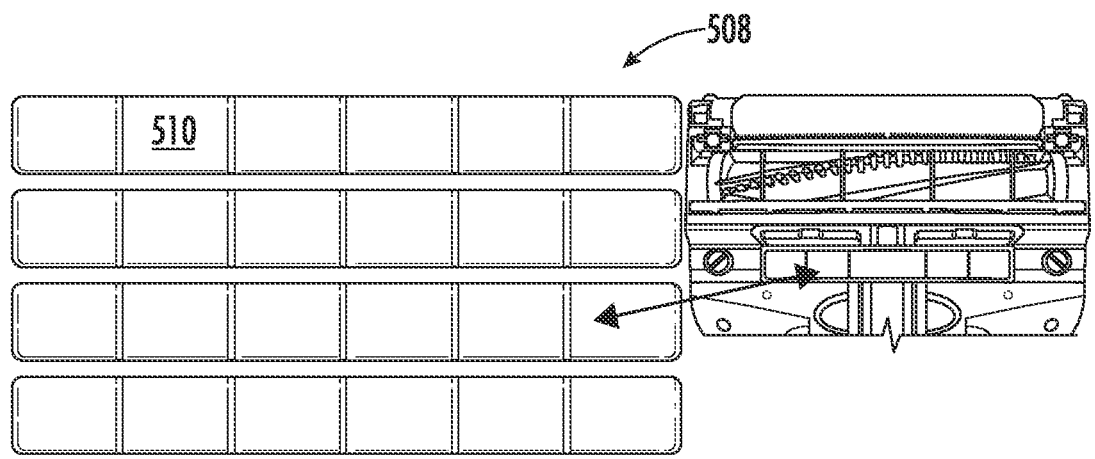
FIG. 6 shows a plurality of example deodorizers consistent with aspects of the present disclosure.

FIG. 6 shows a plurality of example deodorizers 508, which are another example of the deodorizer 208 of FIG. 2. In this example, the deodorizer 508 has an engaging surface 510 and a coupling surface opposite the engaging surface 510. The engaging surface 510 is configured to (directly) engage a surface to be cleaned and the coupling surface is configured to removably couple the deodorizer 508 to a nozzle of a surface cleaning device (e.g., using an adhesive, hook and loop fastening, and/or any other form of removable coupling).

Figures 7, 8:
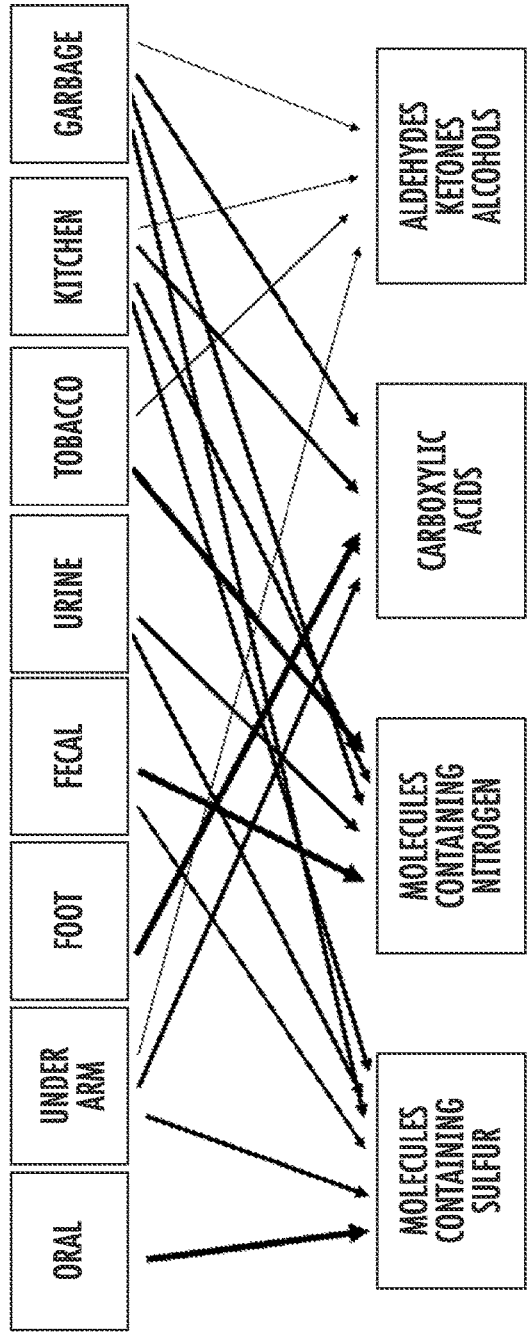
FIG. 7 is a block diagram that maps origins for malodors within a home/office and associated molecule(s) that can cause the malodor.
FIG. 8 shows an example table that shows origins for malodors within a home/office and associated molecule(s) that can cause the malodor.

One aim of the present disclosure is odor management of malodors commonly present in homes. Some such odors include those caused by molecules containing sulfur, molecules containing nitrogen, molecules containing carboxylic acids, and/or molecules containing carbonyl groups (e.g., aldehydes, ketones) or alcohol groups. FIG. 7 graphically maps example origins of malodor and molecule(s) giving rise to those malodors. FIG. 8 is a table that enumerates malodor origins and chemical classifications giving rise to those malodors.

One aspect of the present disclosure has identified compounds formed from long chain fatty acids are particularly well suited for odor control, and in particular, those odors attributable to molecules containing sulfur, nitrogen and/or carbonyl groups. Long chain fatty acids are also negatively charged and can provide an anti-static agent. As used herein, "long chain fatty acid" means a saturated or unsaturated fatty acid having from 12 to 22 carbon atoms, and preferably from 16 to 22 carbon atoms. The long chain fatty acids described herein are saturated and contain from 12 to 22 (or 16 to 22) carbon atoms.

Figure 9:
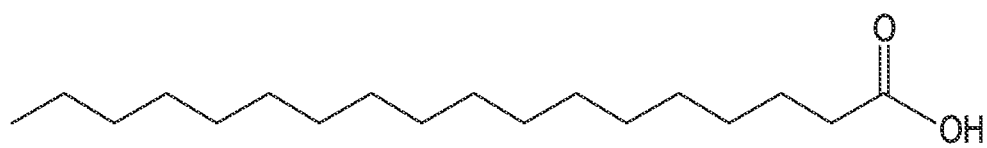
FIG. 9 shows the chemical formula of stearic acid.

Experimental results have demonstrated that stearic acid is particularly well suited for minimizing or otherwise reducing malodors from surfaces such as carpets. Indeed, the inventors have found that application of stearic acid to a surface such as a carpet tends to soften carpet fibers as well as mitigate/prevent static buildup. FIG. 9 shows an example chemical composition of stearic acid and how the same has a carboxylic acid group head and a long hydrocarbon chain tail.

With the foregoing in mind, one aspect of the present disclosure relates to deodorizers for use with cleaning devices, and surface cleaning devices including the same. The deodorizers described herein may be formed from or include (e.g., the deodorizing composition 442, 612 includes) a deodorizing composition. The deodorizing composition may be formed from or include a deodorizing agent, either alone or in combination with a carrier material and one or more optional additives.

Non-limiting examples of suitable deodorizing agents include long chain fatty acids (e.g., stearic acid), Lewis acid-base adducts (see, FIG. 10), a metallic salt such as aluminium chlorohydrate, sodium bicarbonate, zinc ricinoleate ($Zn^{2+}$), combinations thereof, and the like.

In one example, the deodorizing agent consists, consists essentially of, or includes a long chain fatty acid, such as but not limited to stearic acid. In other examples, the deodorizing agent consists, consists essentially of, or includes a metallic salt, such as but not limited to zinc ricinoleate. And, in still further examples, the deodorizing agent consists, consists essentially of, or includes a combination of a long chain fatty acid and a Lewis acid-base adduct.

In examples, the deodorizing composition includes a first deodorizing agent and optionally a second deodorizing agent. In such instances, the first deodorizing agent may be or include a long chain fatty acid such as stearic acid, and the optional second deodorizing agent may be configured to target removal of odors resulting from carboxylic acid containing compounds, e.g., metallic salt such as zinc ricinoleate. In some instances, the second deodorizing agent may generally be referred to as an odor control compound. The odor control compound may be, for example, zinc ricinoleate.

Without limitation, in examples the deodorizing composition includes a combination of stearic acid and zinc ricinoleate. The stearic acid provides a first section of a deodorizer and the zinc ricinoleate provides a second section of a deodorizer, with the first and second sections being coupled to each other to form the deodorizing composition. The relative amounts of first and second deodorizing agents in the deodorizing composition may be selected to achieve desired deodorization performance.

For example, the first and second deodorizing agents may each be present in the deodorizing composition in an amount ranging from greater than 0 to less than 100% by weight (weight %) of the deodorizing composition. In examples, the first deodorizing agent (e.g., a fatty acid such as stearic acid) is present in the deodorizing composition in an amount ranging from about 50 to about 99 weight % (e.g., from about 80 to about 99 weight % or from about 90 to about 99 weight %), and the second deodorizing agent (e.g., a metallic salt such as zinc ricinoleate) is present in the deodorizing composition in an amount ranging from greater than 0 to about 20 weight % (e.g., from about 0.5 to about 5 weight % or from about 0.5 to about 2.5 weight %). In examples, the first deodorizing agent (e.g., a fatty acid such as stearic acid) is present in the deodorizing composition in an amount ranging from about 50 to 100 weight % and the second deodorizing agent (e.g., a metallic salt such as zinc ricinoleate) is present in the deodorizing composition in an amount ranging from greater than 0 to about 20 weight %. In examples, the first and second deodorizing agents are present in the deodorizing composition in the above noted amounts and the total amount of the first and second deodorizing agents (either alone or in combination with, for example, a carrier material, if used) equal 100% by weight of the deodorizing composition.

The carrier material is generally configured to adjust the physical properties of the deodorizing composition, and may be selected to achieve a deodorizing composition that can be applied to carpet or fabric without breaking. Non-limiting examples of suitable carrier materials that may be used include soy wax, cetearyl alcohol, paraffin wax, Microcrystalline wax, combinations thereof, and/or the like. In some examples, the carrier material is soy wax, paraffin wax, or a combination thereof.

When used, the carrier material may be present in the deodorizing composition in an amount ranging from greater than 0 to about 99 weight %, such as from greater than 0 to about 90 weight %, greater than 0 to about 80 weight %, or from about 10 to about 80 weight %. In examples, the deodorizing composition includes a first and/or second deodorizing agent in the above noted weight % ranges, with the carrier material making up the balance of the deodorizing composition.

In specific examples, the deodorizing composition includes a combination of a long chain fatty acid such as stearic acid as a deodorizing agent and soy wax or paraffin wax as a carrier material. In such instances, the relative amounts of long chain fatty acid and carrier material may be adjusted to achieve desired physical properties. For example, increasing the amount of fatty acid (e.g., stearic acid) in the deodorizing composition (while decreasing the amount of carrier material) may increase the brittleness of the deodorizing composition, while increasing or decreasing the durability of the deodorizer. In contrast, increasing the amount of carrier material relative to the amount of fatty acid may result in a deodorizing composition that is more easily spread on carpet and/or fabric, but may reduce the durability or useful lifetime of the deodorizer. In examples, the deodorizing composition includes a fatty acid as a deodorizing agent, but does not include a carrier material. In other examples, the deodorizing composition includes a fatty acid as a deodorizing agent and includes a carrier material, where a ratio of fatty acid to carrier material is in a range of, for example, 1:9 to 4:1 or 1:4 to 2:2.

As noted above, the deodorizing compositions described herein may include one or more optional additives, which may be selected to provide or enhance certain performance characteristics of the deodorizing composition. Surfactants, fragrance fixatives, and low odor fragrances (odor level 1.0 or less) are non-limiting examples of optional additives that may be included in the deodorizing composition.

Non-limiting examples of suitable surfactants that may be used include surfactants that increase the substantivity of the deodorizing composition, i.e., the degree to which the deodorizing composition sticks to fabric/carpet. Non-limiting examples of suitable surfactants that can increase or modify the substantivity of the deodorizing composition include cationic surfactants such as dipalmitoylethyl hydroxyethylmonium methosulfate, and/or other quaternary ammonium compounds such as benzethonium chloride, combinations thereof, and the like.

When used, such surfactants may be included in the deodorizing composition.

Without limitation, in examples the deodorizing compositions described herein include a cationic surfactant (e.g., dipalmitoylethyl hydroxyethylmonium methosulfate) in an amount ranging from about 0.01 to about 90 weight %.

Non-limiting examples of fragrance fixatives that may be included in the deodorizing composition include triethyl citrate or diphenylmethane. When used, such fragrance fixatives may be included in the deodorizing composition in an amount ranging from equal to 0.01% to about 20%.

In some examples, deodorizers consistent with the present disclosure include a reinforcement member that can be embedded within or impregnated with the deodorizing composition. The reinforcement member may be used to provide additional structural integrity or other desired physical characteristics.

Non-limiting examples of suitable reinforcement members that can be used include woven and non-woven materials, such as woven and non-woven sheets (e.g., dryer sheets). In non-limiting examples, the deodorizers described herein include a reinforcement member that is formed from or includes a woven or non-woven sheet (e.g., a dryer sheet) that is embedded within or impregnated with other elements of the deodorizing composition described herein. For example, the deodorizer can include a reinforcement member in the form of non-woven (e.g., dryer sheet) that is impregnated with a first and/or second deodorizing agent (e.g., stearic acid, zinc ricinoleate, and combinations thereof), either alone or in combination with one or more optional additives discussed above.

Figure 10:
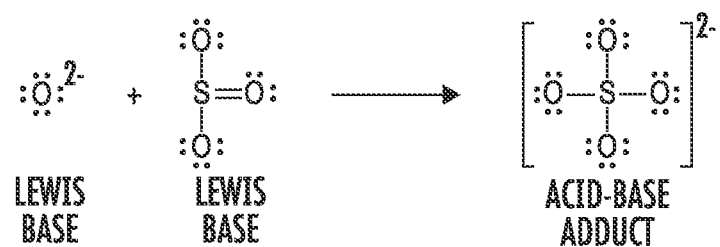
FIG. 10 shows an example of a compound suitable for use as a deodorizing compound consistent with aspects of the present disclosure.

A Lewis acid or electrophilic compound can be added to target molecules containing carboxylic acids. A Lewis acid can be used to counteract malodors by creating an acid-base adduct, such as shown in FIG. 10. FIG. 10 shows an example of an electrophile (also known as a Lewis acid) and a nucleophile (also known as a Lewis base) covalently bonding to form a compound.

Figure 11:
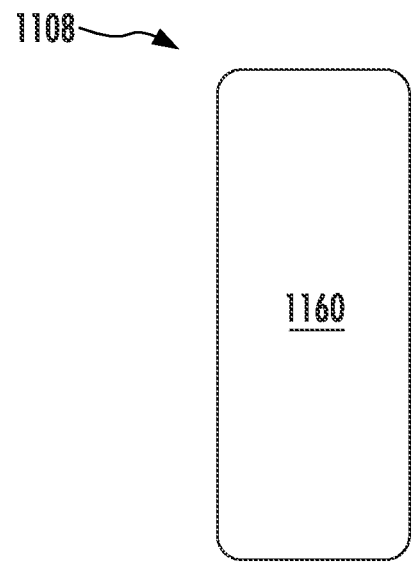
FIG. 11 shows an example deodorizer consistent with aspects of the present disclosure.

FIG. 11 shows an example deodorizer 1108 consistent with aspects of the present disclosure. The deodorizer 1108 can be an example of the deodorizer 208 of FIG. 2. For example, the deodorizer 1108 can be disposed on a bottom surface of a nozzle and can be configured to engage (directly) a surface to be cleaned to release particles for odor management. Alternatively, or in addition, the deodorizer 1108 can be an example of the deodorizer 308 of FIG. 3. For example, the deodorizer 1108 can be configured to engage (directly) an associated cleaning element, such as the second cleaning element 310-2 of FIG. 3.

The deodorizer 1108 may include a first section 1160 formed from a deodorizing composition as noted above. In examples where the deodorizer 1108 consists of the first section 1160, it may be referred to as a single homogenous strip/bar.

In examples, the first section 1160 is formed from (e.g., consists or consists essentially of) or includes a long chain fatty acid such as stearic acid. In specific examples, first section 1160 includes stearic acid, the chemical composition of which is shown in FIG. 9.

In other examples, the first section 1160 includes a fatty acid such as stearic acid, in combination with an acid-base adduct such as zinc ricinoleate. The first section 1160 can define an engagement surface, such as engagement surface 324 of FIG. 3.

The deodorizing composition may be formed in any suitable manner. For example, when the deodorizing composition includes first and second deodorizing agents, formation of the deodorizing composition may include melting the first and second deodorizing agents and then combining the melts with one another.

Alternatively, the first and second deodorizing agents may be mixed within one another (e.g., as solid particulates) and then melted together to form a melt containing both the first and second deodorizing agents. The carrier and optional additives noted above can be combined with the deodorizing agent(s) in any suitable manner, e.g., by melting them separately or with the deodorizing agent(s). When the deodorizing agent(s) and other components are combined to form a melt, the melt may be molded into a form that can be used as or in the deodorizer 1108. Alternatively, or additionally, when a reinforcement member is used, the reinforcement member may be embedded in or impregnated with the melt in any suitable manner. In such instances, the reinforcement member may be selected to provide additional structural integrity/strength to the deodorizer 1108.

The deodorizer 1108 may have an overall volume in a range of 20 milliliters (ml) to 80 ml. The deodorizer 1108 may have an overall height in a range of 5 mm to 25 mm, an overall length in a range of 100 mm to 280 mm and an overall thickness in a range of 5 mm to 25 mm.

Figure 12:
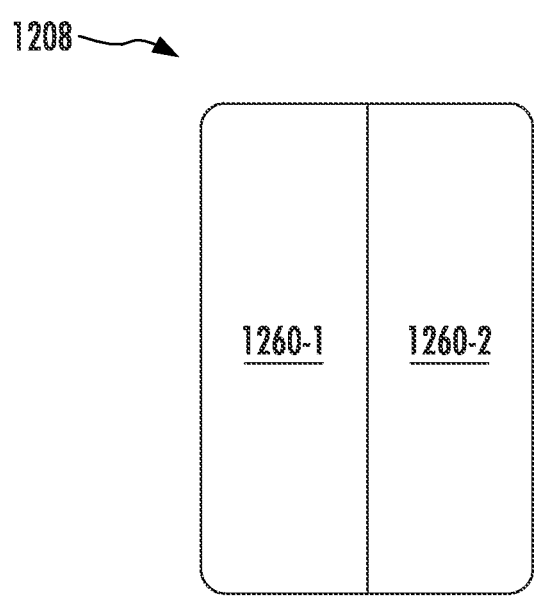
FIG. 12 shows another example deodorizer consistent with aspects of the present disclosure.

FIG. 12 shows another example deodorizer 1208 consistent with the present disclosure. The deodorizer 1208 can be an example of the deodorizer 208 of FIG. 2. For example, the deodorizer 1208 can be disposed on a bottom surface of a nozzle to engage (directly) a surface to be cleaned to release particles for odor management. Alternatively, or in addition, the deodorizer 1208 can be an example of the deodorizer 308 of FIG. 3. For example, the deodorizer 1208 can be configured to engage (directly) an associated cleaning element, such as the second cleaning element 310-2 of FIG. 3.

The deodorizer 1208 includes a first portion/section 1260-1 formed from a first material and a second portion 1260-2 formed from a second material, wherein the first and second materials differ from each other. The first material may include a first deodorizing agent and a carrier, and the second material may include a second deodorizing agent and a carrier, wherein the first deodorizing agent, second deodorizing agent, and carrier are selected from the compositions noted above. Without limitation, the first material may consist, consist essentially of, or include a combination of a long chain fatty acid such as stearic acid with a carrier material such as paraffin wax, soy wax and/or cetearyl alcohol, and the second material may consist, consist essentially of, or include a combination of a metallic salt such as zinc ricinoleate and a carrier such as paraffin wax, soy wax, and/or cetearyl alcohol. The first portion 1260-1 may include a combination of stearic acid and a carrier material (e.g., paraffin wax). The second portion 1260-2 may include zinc ricinoleate in range of 0.5 to 20 weight %, the remainder of second portion 1260-2 being a carrier material (e.g., paraffin wax) in a range of 80 to 99.5 weight %.

The first portion 1260-1 and the second portion 1260-2 can be configured to couple together and form a single monolithic structure. The first portion 1260-1 and the second portion 1260-2 can be coupled together via, for instance, an adhesive coupling, a mechanical coupling, and/or any other form of coupling.

The deodorizer 1208 may have an overall volume in a range of 20 ml to 80 ml. The deodorizer 1208 may have an overall height in a range of 5 mm to 25 mm, an overall length in a range of 100 mm to 280 mm and an overall thickness in a range of 5 mm to 25 mm.

The first portion 1260-1 and the second portion 1260-2 can include identical or different dimensions. The first portion 1260-1 and the second portion 1260-2 can include the same or different shape/profiles.

The first portion 1260-1 may have an overall volume in a range of 10 ml to 70 ml. The first portion 1260-1 may have an overall height in a range of 5 mm to 25 mm, an overall length in a range of 100 mm to 280 mm, and an overall thickness in a range of 2.5 mm to 20 mm.

The second portion 1260-2 may have an overall height in a range of 5 mm to 25 mm, an overall length in a range of 100 mm to 280 mm, and an overall thickness in a range of 2.5 mm to 20 mm.

As discussed above, the first portion 1260-1 can be formed using a process similar to the process discussed above with regard to FIG. 11. The second portion 1260-2 can be formed by melting a deodorizing agent and carrier together. This melt can be either poured into a separate mold to cool in a similar way to forming the first portion 1260-1 or poured into the same mold as the first portion 1260-1 (e.g., over the top of the solidified/cooled first portion).

The example of FIG. 12 may also be referred to as a multi-action strip/bar. The multi-action strip may include at least two different portions/sections such as the first portion 1260-1 and the second portion 1260-2. The at least two different sections can be coupled together and form an interface therebetween. Forming the deodorizer 1208 can include forming each section separately and allowing each to cool, e.g., to room temperature. The two cooled sections may then be coupled together as shown in FIG. 12. Alternatively, a first section may be formed and cooled. Once cooled, a second section may then be disposed on the first section and cooled.

The deodorizer 1208 can include a multi-action configuration where each section targets a different group/classification of malodor molecules. For example, the first portion 1260-1 targets molecules containing sulfur, aldehydes, ketones and alcohols based on the long chain fatty acid, e.g., stearic acid, and the second portion 1260-2 targets molecules containing carboxylic acid based on the odor eliminating compound, e.g., zinc ricinoleate.

In a scenario where stearic acid is included in the first portion 1260-1 and zinc ricinoleate is included in the second portion 1260-2, the interface may advantageously isolate each section to limit the deactivation of the zinc ricinoleate to the region forming the interface. As is known, zinc ricinoleate can be deactivated based on a chemical interaction of the carboxylic acid head of the stearic acid binding/using up active sites in the zinc ricinoleate.

In operation, each section/portion of the deodorizer 1208 is in contact (direct) with the surface to be cleaned and/or an associated cleaning element, such as the second cleaning element 310-2 (see, FIG. 3).

FIG. 13 shows example material combinations for the deodorizer 1108 (see, combinations 1-25) and for the multi-action (MA) configuration of the deodorizer 1208.

One particular formulation that was found to be particularly well suited for forming a deodorizing composition odor was 80 weight % Steric Acid with 20 weight % Soy Wax, combined with 10% Zinc Ricinoleate and 90% Soy Wax.

Selection of a formulation for a deodorizer consistent with the present disclosure may provide one or more of the following: a deodorizer that can be mechanically engaged to output a predetermined amount of particles (e.g., in a range of 0.01 to 1.00 grams per hour for at least fifteen hours of operation of a cleaning device); a deodorizer that is chemically stable in water; a deodorizer that is safe to contact human skin and stable in contact with household surfaces; a deodorizer that does not chemically react to household cleaning chemicals such as vinegar or bleach; a deodorizer whose released particles will not cause damage to a surface to be cleaned and, should the particles accumulate on a surface, those cumulative particles do not negatively impact the look or feel of the surface, such as a carpet, nor damage floor surfaces such as hard woods, e.g., by de-stabilizing floor glue/applicator; and/or a deodorizer whose released particles will not damage parts/components within the surface cleaning device and/or cause discoloration/staining.

Deodorizers consistent with the present disclosure were tested with different compound configurations as shown in the table of FIG. 14 to determine relative durability. Strips/bars with a greater concentration of stearic acid were found to be generally harder/rigid and therefore demonstrated a relatively high amount of durability relative to other compound configurations.

Each test sequence included the following steps: (1) weigh strip/bar to determine initial weight in grams (g); (2) place strip/bar into direct contact with soft brush bar (or foam roller implemented as the second cleaning element 310-2 in FIG. 3) ensuring contact between the strip/bar and soft brush bar or foam roller remains throughout the duration of the test. This test can be performed with either gravity and/or a spring member exerting a force (F1, FIG. 3) on the strip/bar. In the example shown in table in FIG. 14, a spring force was used and supplied a bias force; (3) operate surface cleaning device for ten minutes, during which the surface cleaning device remains stationary and the associated cleaning element is rotated while in direct contact with the strip/bar (e.g., see FIG. 3); (4) weigh the strip/bar after the ten minutes, and note new weight in grams; (5) determine overall weight loss in grams by subtracting the new weight from the original weight; (6) extrapolate difference between initial weight and weight after ten minutes of use to determine six month loss value and hourly rate of use/loss values.

Example compounds for use within a deodorizer consistent with the present disclosure include zinc ricinoleate, Dipalmitoylethyl hydroxyethylmonium methosulfate (Cationic surfactant) to increase substantivity to fabric (e.g., how much it sticks to fabric/carpet), fragrance fixatives such as triethyl citrate, diphenylmethane, and/or a low odor fragrance chemical such as citral or limonene.

Various features and aspects of the present disclosure may be implemented in both powered and unpowered surface cleaning devices. Powered surface cleaning devices refer to a surface cleaner configured to drive/energize at least one cleaning element, such as a suction motor and/or brush roll, based on a DC and/or AC power signal. Some such examples of powered surface cleaning devices include robotic vacuums and cannister vacuums.

Unpowered surface cleaning devices refer to surface cleaning devices that perform a cleaning operation without generating an electrical load, e.g., on a battery or AC mains. Such unpowered surface cleaning devices can include a carpet sweeper that utilizes a mechanical assembly to collect debris based on a user-supplied force (or manual force) that causes forward/backward movement of the carpet sweeper against a surface to be cleaned.

The present disclosure also recognizes that in some scenarios a powered surface cleaning device having a deodorizer consistent with the present disclosure may be used in an unpowered/manual mode when odor management is desired. For instance, a surface cleaning device consistent with the present disclosure may be pushed/pulled by a user when the surface cleaning device is powered off/deenergized to cause the odor member to be mechanically engaged via the surface to be cleaned and/or cleaning element (e.g., a brush roll). This mechanical engagement can cause the deodorizer to release particles onto the surface to be cleaned and/or into the surrounding area for odor management without requiring battery power to be consumed, or requiring the surface cleaning device to be plugged into an electrical outlet via a power cord.

An example of a surface cleaning device, consistent with the present disclosure, may include a nozzle, a dust cup, a suction motor configured to draw air into the nozzle and through the dust cup, and a first deodorizer coupled to the nozzle, the first deodorizer includes a deodorizing composition having a long chain fatty acid.

In some instances, the long chain fatty acid may be a stearic acid. In some instances, the deodorizing composition may be 50 to 100 weight % stearic acid. In some instances, the first deodorizer may include a first portion formed of the long chain fatty acids and a second portion formed of an odor control compound. In some instances, the odor control compound may include zinc ricinoleate. In some instances, the deodorizing composition may include a carrier material. In some instances, the carrier material may include paraffin wax. In some instances, the first deodorizer may be configured to directly engage a surface to be cleaned during cleaning operations. In some instances, the nozzle may include a cleaning element and the first deodorizer engages the cleaning element. In some instances, the cleaning element may be a foam roller. In some instances, a second deodorizer may be coupled to the nozzle. In some instances, at least one of the first deodorizer or the second deodorizer may be configured to directly engage a surface to be cleaned. In some instances, the nozzle may include a cleaning element and at least one of the first deodorizer or the second deodorizer is configured to directly engage the cleaning element. In some instances, the cleaning element may be a brush roll or a foam roller. In some instances, the first deodorizer may be removably coupled to the nozzle. In some instances, the first deodorizer may include a cartridge body. In some instances, the nozzle may include a cartridge receptacle configured to receive the cartridge body. In some instances, the cartridge receptacle may include a latch configured to releasably engage the cartridge body. In some instances, surface cleaning device may include further include a plurality of cleaning elements. In some instances, at least one cleaning element may be different from at least one other cleaning element.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. It will be appreciated by a person skilled in the art that a surface cleaning apparatus may embody any one or more of the features contained herein and that the features may be used in any particular combination or sub-combination. Modifications and substitutions by one of ordinary skill in the art are considered to be within the scope of the present disclosure, which is not to be limited except by the claims.

What is claimed is:

1. A surface cleaning device comprising:
    a nozzle;
    a first rotating agitator rotatably coupled to the nozzle, the first rotating agitator configured to rotate about a first longitudinal axis; and
    a first deodorizer coupled to the nozzle and configured to directly contact an outer surface of the first rotating agitator as the first rotating agitator rotates about the longitudinal axis, the first deodorizer includes a deodorizing composition having a long chain fatty acid.

2. The surface cleaning device of claim 1, wherein the long chain fatty acid is a stearic acid.

3. The surface cleaning device of claim 2, wherein the deodorizing composition is 50 to 100 weight % stearic acid.

4. The surface cleaning device of claim 1, wherein the first deodorizer includes a first portion formed of the long chain fatty acids and a second portion formed of an odor control compound.

5. The surface cleaning device of claim 4, wherein the odor control compound comprises zinc ricinoleate.

6. The surface cleaning device of claim 1, wherein the deodorizing composition comprises a carrier material.

7. The surface cleaning device of claim 6, wherein the carrier material comprises paraffin wax.

8. The surface cleaning device of claim 1, wherein the first rotating agitator is a foam roller.

9. The surface cleaning device of claim 1, further comprising a second deodorizer coupled to the nozzle.

10. The surface cleaning device of claim 9, wherein the second deodorizer is configured to directly engage a surface to be cleaned.

11. The surface cleaning device of claim 1, wherein the first deodorizer is removably coupled to the nozzle.

12. The surface cleaning device of claim 11, wherein the first deodorizer includes a cartridge body.

13. The surface cleaning device of claim 12, wherein the nozzle includes a cartridge receptacle configured to receive the cartridge body.

14. The surface cleaning device of claim 13, wherein the cartridge receptacle includes a latch configured to releasably engage the cartridge body.

15. The surface cleaning device of claim 1 further comprising a second rotating agitator.

16. The surface cleaning device of claim 15, wherein the first rotating agitator is different from the second rotating agitator.

17. The surface cleaning device of claim 15, further comprising:
    a dust cup; and
    a suction motor;
    the nozzle further including a front side, a back side, and an opening on an underside of the nozzle between the front side and the back side, the opening fluidly coupled to the suction motor;
    wherein the second rotating agitator is mounted to the nozzle within the suction conduit and configured to rotate about a second longitudinal axis; and
    wherein the first rotating agitator is closer to the front of the nozzle than the second rotating agitator.

18. The surface cleaning device of claim 17, wherein the first rotating agitator is a foam roller and the second rotating agitator is a brush roll.

19. The surface cleaning device of claim 1, wherein the first deodorizer includes an engagement surface configured to directly contact the outer surface of the first rotating agitator.

20. The surface cleaning device of claim 19, wherein the engagement surface includes a profile that corresponds with a profile of the first rotating agitator.

* * * * *